| United States Patent [19] | [11] Patent Number: 5,013,645 |
| Kim | [45] Date of Patent: May 7, 1991 |

[54] IMMUNOLOGICAL METHODS AND MATERIALS FOR DETECTION OF TUMOR ASSOCIATED ANTIGENS

[75] Inventor: Yung D. Kim, Libertyville, Ill.

[73] Assignee: Abbott Laboratories, North Chicago, Ill.

[21] Appl. No.: 166,059

[22] Filed: Mar. 23, 1988

Related U.S. Application Data

[63] Continuation-in-part of Ser. No. 38,129, Apr. 14, 1987, abandoned.

[51] Int. Cl.$^5$ .................. G01N 33/53; G01N 33/543; C07K 15/14; C12N 15/00
[52] U.S. Cl. .................... 435/7.92; 435/69.3; 435/172.2; 435/240.27; 435/810; 435/7.23; 436/501; 436/518; 436/536; 436/538; 436/548; 436/64; 436/808; 436/813; 530/395; 530/413; 530/828; 530/387; 935/103; 935/110
[58] Field of Search ............. 435/7, 68, 172.2, 240.27, 435/810, 69.3, 69.6; 436/548, 813, 808, 545, 546, 501, 518, 536, 538, 64; 530/387, 395, 413, 828; 424/85; 935/107, 110, 103, 106

[56] References Cited

U.S. PATENT DOCUMENTS

| 4,446,122 | 5/1984 | Chu et al. ........................ 435/4 |
| 4,612,282 | 9/1986 | Schlom et al. .................. 435/172.2 |
| 4,707,438 | 11/1987 | Keydar ............................ 435/5 |

FOREIGN PATENT DOCUMENTS

0118365  9/1984  European Pat. Off. .
7900475  7/1979  PCT Int'l Appl. .

OTHER PUBLICATIONS

Papsidero et al, Cancer Research, vol. 43, Apr. 1983, pp. 1741–1747.
Safi et al, Cancer, vol. 57(4), Feb. 1986, pp. 779–783.
Del Favero et al, Cancer, vol. 57(8), Apr. 1986, pp. 1576–1579.
Gupta et al, Cancer, vol. 56(2), Jul. 1985, pp. 277–283.
Wright et al, Cancer Research, vol. 43, Nov. 1983, pp. 5509–5516.
Ware et al, Cancer Research, vol. 42, Apr. 1982, pp. 1215–1222.
Del Villano et al, Clin. Chem., vol. 29/3, 1983, pp. 549–552.
Sekine et al, The J. of Immunology, vol. 135(5), Nov. 1985, pp. 3610–3615.

*Primary Examiner*—Esther L. Kepplinger
*Assistant Examiner*—Florina B. Hoffer

[57] ABSTRACT

Disclosed are immunological methods and materials for detection of antigens associated with breast or prostate cancer disease states. Presently preferred antibody preparations (e.g., PR92 monoclonal antibodies produced by hybridoma cell line ATCC HB 9390) are employed in immunoassays performed on patient body fluids and for purification of tumor-associated antigen compositions.

15 Claims, 6 Drawing Sheets

PR92, PAP AND PA LEVELS OF TRACKING SERA OF A PROSTATE CANCER PATIENT

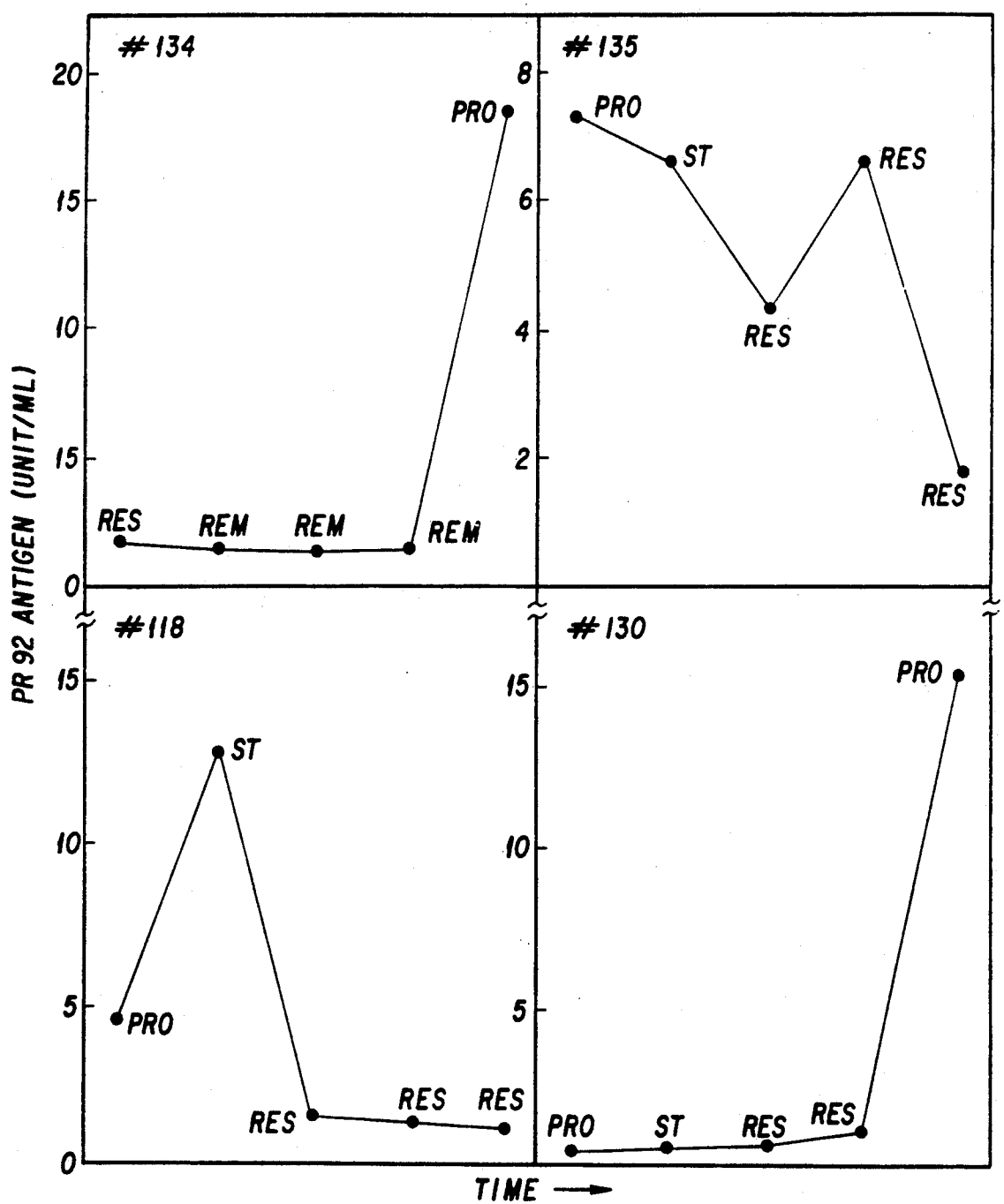

IMMUNOLOGICAL METHODS AND MATERIALS FOR DETECTION OF TUMOR ASSOCIATED ANTIGENS

This is a continuation-in-part of Ser. No. 038,129, filed Apr. 14, 1987, now abandoned.

FIELD OF INVENTION

The present invention relates generally to methods and materials useful in immunological procedures for the diagnosis and clinical monitoring of carcinomas and other types of malignancy. More specifically, the invention relates to novel antibody and antigen preparations and their use in procedures for detecting and monitoring prostatic or breast tumor disease states.

BACKGROUND

Immunological technologies have provided for major advances in therapeutic and diagnostic techniques in cancer diagnosis and both in vitro and in vivo cancer therapy. Numerous tumor-associated antigens have been characterized and polyclonal and monoclonal antibodies specifically immunoreactive with such have been proposed for use as diagnostic and prognostic aids in the clinical management of tumor disease states.

Of interest to the background of the invention are references generally relating to useful monoclonal antibodies raised against human tumor cells (see, e.g., Chen, U.S. Pat. No. 4,618,585) and especially the following references generally relating to monoclonal antibodies immunoreactive with various tumor-associated antigens such as CA 19-9, CA 125 and carcinoembryonic antigen (CEA) and to diagnostic tests based on the use of one or more of such antibodies: Del Villano, WO 84/00758 (CA 19-9); Safi, et al., Cancer, 5, 779–782 (1986) (CA 19-9); Brochure published by Centocor, "Carbohydrate Antigen 19-9 Radioimmunoassay", (1983) (CA 19-9); Del Villano, et al., Clin. Chem., 29 3, 549–552 (1983) (CA 19-9); De Favero, et al., Cancer, 57, 1576–1579 (1986) (CA 19-9); Gupta, et al., Cancer, 56, 277–283 (1985) (CA 19-9); Brochure published by Centocor relating to CA 125, (1983); Bergmann, et al., Cancer, 59, 213–217 (1987) (CA 125); Pinto, et al., Cancer, 59, 218–222 (1987) (CA 125); Brochure published by Centocor relating to CA 19-9 and CEA (1984); and Bast, et al., New Eng. J. Med., 309/15, 883–920 (1983) (CA 125); Brochure published by Centocor, "Centocor Cancer Antigen 125 TM ) Radioimmunoassay" (1983) (CA 125); Bast, et al., Am. J. Obstet. Gynecol., 149/5, 553–559 (1984) (CA 19-9, CA 125, and CEA).

Of interest to the background of the present invention are the following references relating to the diagnosis of prostate cancer disease states on the basis of elevated levels of marker substances such as "prostate specific antigen" (PA) and prostatic acid phosphatase (PAP) which are present in low levels in normal human serum and the serum of patients with benign prostatic hyperplasia, but present at higher levels in sera of prostatic carcinoma patients, especially those in an advanced disease state: Lin, et al., U.S. Pat. No. 4,298,592; Lee, et al., U.S. Pat. No. 4,267,272; Miller, et al., U.S. Pat. No. 4,510,239; and, European Patent Application No. 160228 published Nov. 6, 1985.

Of substantial interest to the background of the invention with respect to immunological methods for diagnosis of prostate cancer are the following references relating to monoclonal antibodies raised against human prostate tumor cell lines PC-3 and DU145: Ware, et al., Cancer Research, 42, 1215–1222 (April 1982) (PC-3); Raynor, et al., J.N.C.I., 73, 617–625 (1984) (PC-3); Carroll, et al., Clinical Immunology and Immunopathology, 33, 268–281 (1984) (PC-3); Starlinq, et al., Cancer Research, 42, 3084–3089 (1982) (DU-145); Starling and Wright, Cancer Research, 45, 804–808 (1985) (DU-145); and Wright, et al., Cancer Research, 43, 5509–5516 (1983) (PC-3 and DU-145).

Also of interest to the background of the invention are the following references relating to the diagnosis of breast cancer disease states on the basis of monoclonal antibodies raised against various breast tumor cell lines and breast tissues: Schlom, et al., U.S. Pat. No. 4,612,282; Hilkens, et al., Prot. Bio Fluids. 29, 813–816 (1981); Hilkens, et al., Prot. Bio. Fluids, 31, 1013–1016 (1984); Dempsey, et al., J.N.C.I., 77, 1–9 (1986); Papsidero, et al., Cancer Research, 43, 1741–1747 (1983); Brochure published by Centocor, "Centocor CA 15-3 Radioimmunoassay" (1985); Brochure published by Centocor, "Radioimmunoassay for the Detection of CA 15-3 in Serum or Plasma" (1986) and the further references cited therein; Hilkens, et al., Int. J. Cancer, 34, 197–206 (1984); Kofe, et al., Hybridoma, 3, 223–232 (1984); Sekine, et al., J. Immunology, 135 3610–3615 (1985); and, Schmidt-Rhode, et al., International Society for Oncodevelopmental Biology and Medicine, Sept. 10–13, Paris, 1985.

Despite the above noted advances in the art, there continues to exist a need for methods and materials useful in accurately detecting and monitoring prostate or breast tumor disease states.

BRIEF SUMMARY

The present invention provides novel means for determining the presence of prostate or breast cancer disease states in human patients through analysis of patient body fluid samples for the presence of one or more antigens specifically immunoreactive with the monoclonal antibody ("PR92 Mab") produced by the novel murine derived hybridoma cell line ATCC HB 939. In presently preferred forms, patient serum or urine samples are analyzed by immunoassay techniques such as radioimmunoassays, fluorescent immunoassays, or enzyme-linked immunosorbent assays in either direct or competitive formats.

In another of its aspects, the present invention provides novel hybridoma cell lines (exemplified by murine-derived cell line ATCC HB 9390) and novel monoclonal antibodies secreted thereby (exemplified by the above-noted PR92 Mab). Antibodies of the invention are provided in whole or fragment form and may be unlabeled or labeled with suitable detectable immunoassay markers such as radiochemicals (e.g., $I^{125}$), enzymes or fluorescent compounds.

In a preferred assay procedure of the invention, unlabeled antibodies of the invention are immobilized on a solid substrate and incubated with a body fluid sample to form a first reaction mixture comprising sample antigens associated with prostate and breast cancer disease states bound to the antibodies. Following removal of unbound sample components (by, e.g., washing) the first reaction mixture is incubated with labeled antibodies to form a second reaction mixture wherein labeled antibodies are immobilized by reaction with bound sample antigens. Following removal of unbound labeled antibodies from the second reaction mixture, the mixture is analyzed to detect the extent to which labeled antibodies have been bound. Assay kits according to the invention are thus seen to generally comprise both labeled and unlabeled antibodies of the invention, preferably unlabeled and $I^{125}$ labeled monoclonal antibodies produced by hybridoma cell lines ATCC HB 9390.

Antibodies of the invention are suitable for use in assays allowing determination of the relative efficacy of a therapeutic regimen applied to a patient suffering from a prostate or breast cancer disease state and in assays useful to detect recurrence of such cancers in patients who have been clinically diagnosed as being in a stabilized or remissive state.

According to another aspect of the invention there are provided purified and isolated tumor associated antigen compositions ("PR92 antigens") characterized by their specific immunological reactivity with the PR92 Mab produced by ATCC HB 9390. Presently, the antigen compositions are most readily purified from human pleural fluids of cancer patients, or are isolated from DU145 tissue culture media or from DU145 cell extracts. The antigen compositions are characterized by a non-reduced molecular weight of up to about $480\pm10$ kD and a reduced molecular weight of about 47 kD. The antigens are further characterized as glycoproteins including sialic acid, N-acetyl-beta-D-galactosamine and beta-D-galactose moieties. Antibodies, including monoclonal antibodies, raised against and immunologically reactive with the PR92 antigen composition are also within the contemplation of the invention.

Numerous other aspects and advantages of the present invention will be apparent upon consideration of the following detailed description including illustrative examples of presently preferred embodiments thereof.

BRIEF DESCRIPTION OF FIGURES

FIGS. 1, 2, 3 and 6 provide graphic representations of results of analysis of patient sera for PR92 Mab reactive substances (PR92 antigens) and FIGS. 4 and 5 provide graphic representations of the results of patient serum analysis for PR92 Mab reactive substances, as well as, analysis for prostate specific antigen and prostatic acid phosphatase.

DETAILED DESCRIPTION

Figure 1:
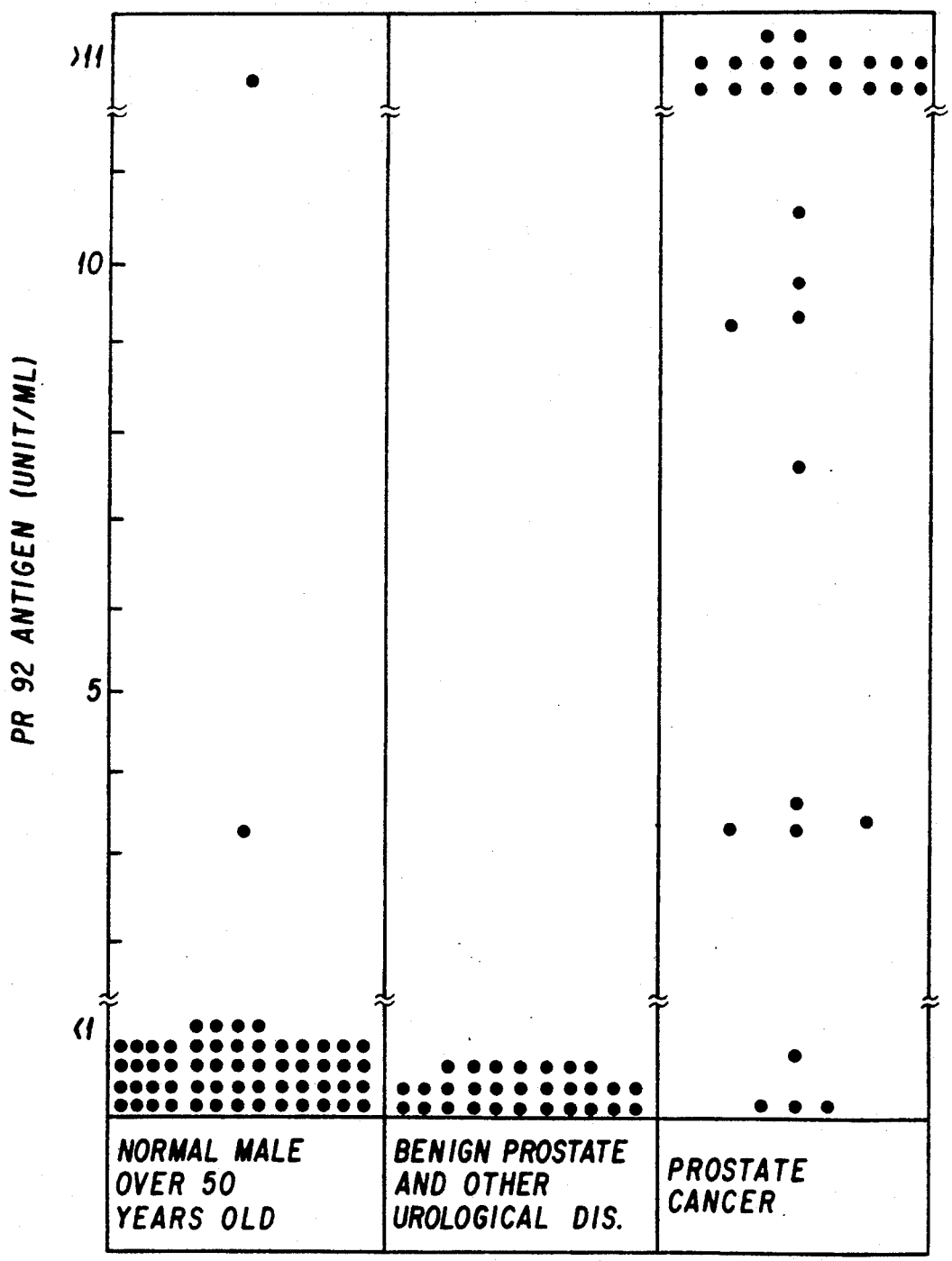

The following illustrative examples relate to the development of monoclonal antibodies which specifically react with tumor associated antigens found in body fluids of individuals with breast or prostate cancer. More specifically, Example 1 relates to the procedures whereby hybridoma cell lines secreting monoclonal antibodies were generated. Example 2 relates to characterization of antibodies produced by a selected hybridoma cell line. Example 3 relates to a radioimmunoassay based on a selected monoclonal antibody and use of this radioimmunoassay in screening for reactivity with known tumor-associated markers. Examples 4, 5, 6, 7 and 8 relate to immunoassay techniques applied to the measurement of antigens in fluid samples of prostate and breast cancer patients. Example 9 relates to immunopurification and characterization of PR92 antigen compositions. Example 10 relates to the use of the PR92 Mab radioimmunoassay procedure as an aid in the diagnosis and prognosis of cancer patients. Examples 11, 12 and 13 relate to the production of PR92 antigen from cells and tissue cultures.

EXAMPLE 1

Female Balb/C mice were immunized by injection of viable DU145 prostate cancer cells obtained from the American Type Culture Collection, 12031 Parklawn Drive, Rockville, Md. as ATCC HTB 81. The mice were injected once per week with $10^7$ viable cells for four weeks. Blood samples from each mouse were assayed for antibodies to DU145. More specifically, sera were added to microtiter plates coated with sonicated DU145 cell products fixed with gluteraldehyde. Enzyme-conjugated goat anti-mouse IgG indicated a positive reaction when a colored solution was formed. Upon a showing of a positive reaction between a serum sample and the DU145 cell line a hyperimmunization injection of $10^7$ DU145 cells was given to the mouse and one week later the mice were sacrificed and their spleens removed for culturing purposes.

Three different culture media were employed in hybridoma production. Medium A consisted of Dulbecco's Minimal Essential Medium (DMEM) with 2.0 mM L glutamine, and 50 $\mu$g/ml Gentamycin. Medium B consisted of Medium A with the addition of 20% fetal calf serum. Medium C consisted of Medium B with $1\times10^{-4}$M hypoxanthine, $4\times10^{-7}$M aminopterin and $3\times10^6$M thymidine. Costar (Cambride, Mass.) microtitre plates #3524 and #3596 were used.

Spleen cells were prepared by squeezing the tissue through a wire screen into Solution A. After centrifugation, the red cells were lysed by suspending the pellet in 2 ml of 0.83% ammonium chloride in 10 mM Tris. After centrifugation the pellet was resuspended in solution A. The mouse spleen cells were then fused with cells from the mouse myeloma cell line SP2/0-Ag14 according to the procedure of De St. Groth, et al., *J. Immunol. Methods*, 35, 1-21 (1980), with approximately $1-1.5\times10^8$ spleen cells mixed with an equal number of SP2/0-Ag14 melanoma cells in a 50 ml conical centrifuge tube. After centrifugation at 1400 rpm for 5 minutes the supernatant was removed and 1.0 ml of 50% v/v polyethyleneglycol (PEG)-DMEM (MW 1000, Sigma Chemicals) was added to the cell pellet. The cells were resuspended and after addition of 1 ml of solution A were allowed to stand for 1 minute. Twenty ml of medium A were added slowly over the next 3-5 minutes. The cells were centrifuged at 1400 rpm for 5 minutes, the supernatant aspirated and the cells resuspended in 20 ml medium C. The cell suspension was then transferred to 75 cm$^3$ T-flasks and incubated for 1-3 hours at 37° C. in a CO$_2$ incubator.

The fused cell mixtures were diluted to $1\times10^6$ cells/ml with medium C. A one tenth ml volume of cell suspension was pipetted into each well of 24 well microtitre plates and incubated at 37° C. and 5% CO$_2$ for 24 hours. A one tenth ml volume of spleen feeder cells suspended in medium C at a density of $2-3\times10^5$ cells/ml was added to each well and the cultures were incubated at 37° C., 5% CO$_2$ for 14-17 days.

On every other day during the period of incubation, 1 ml of medium was aspirated from each well and replaced with 1 ml of fresh medium C. Assaying the supernatant of hybridoma containing wells for antibody production began about day 10 to 12.

Hybridoma colonies which produced antibodies exhibiting strong specificity to the DU145 cell line were selected for further propagation to obtain pure clones for amplification. The cells in antibody positive wells were diluted in a volume of medium B to a concentration of 10 cells/ml. One tenth ml volumes of cell suspension and one tenth ml volumes of spleen feeder cells in medium B at a concentration of $5 \times 10^5$ cells/ml were transferred into microtitre wells of Costar plates. The plates were incubated at 37° C. and 5% $CO_2$ for 14 days during which time single cells grew to sizeable clones. Supernatant solutions were assayed for antibody production. Antibody-producing clones were expanded without feeder cells in Costar plates and eventually in T-flasks.

The hybridoma clones were screened against DU145, human fetal kidney (HFK) cell extracts, CEA and PAP antigens. Sixteen hybridomas exhibiting strong binding with the DU145 cell line and essentially no binding with HFK cell extracts, CEA or PAP were then selected to be grown in vivo. Balb/C females were injected intraperitoneally with $45 \times 10^6$ hybridoma cells. The ascites fluid suspensions were passed every 7–10 days. Antibodies of the 16 clones were further assayed for binding specificity using tumor cell lines listed in Table I.

TABLE I

| Tissue Culture Cell Lines Tested With Hybridoma Supernatant | |
|---|---|
| PROSTATE CANCER: | DU145, PC-3 |
| NORMAL CELL: | ABH, LYMPHOCYTES, HUMAN FETAL KIDNEY |
| BLADDER CANCER: | T24, J82, HT1197, HT1376, 647V, RT4. |
| PANCREATIC CANCER: | MIA. |
| LUNG CANCER: | A549, CHAGO. |
| COLON CANCER: | DLD-1. HT29 |
| BREAST CANCER: | MOA-MB, BT20. |
| CERVIX CANCER: | C33A. |
| RENAL CANCER: | ACHN |
| UTERINE CANCER: | SKUT-1B, |

Results for antibodies of the five clones non-reactive with normal cell extracts and least cross-reactive with other types of cells derived from malignant tissues are shown in Table II.

TABLE II

| Binding Studies With Selected Clones Against the Cell Lines of Table I | |
|---|---|
| Selected Clone | Reactive Cell Lines |
| H23C163 | DU145, PC-3, J82, A549, CHAGO, MOA-MB. |
| H29C138 | DU145, CHAGO. |
| H65C137 | DU145, T24, J82, MIA, CHAGO, HT1376, MOA-MB, BT20. |
| H92C149 | DU145, CHAGO. |
| H92C152 | DU145, CHAGO. |

Combinations of these five antibodies were employed as the bottom layer and/or top layer in a sandwich type radioimmunoassay (as described in Example 3, infra.) using a panel of serum and urine samples from normal, benign disease and malignant disease patient populations. The monoclonal antibody produced by cell line H92C149 in combination with itself demonstrated superior sensitivity and specificity in detecting antigens in serum and urine specimens from prostate and breast cancer patients.

Cell line H92C149 was deposited with the American Type Culture Collection, Rockville, Md. on Apr. 10, 1987, under deposit accession number HB 9390.

EXAMPLE 2

Characterization of the Monoclonal Antibody Produced by Cell Line ATCC HB 9390

In order to type the heavy chain of the monoclonal antibody produced by cell line ATCC HB 9390, purified antibody (40 ng/ml) in 0.01M Tris, at pH 8 was added to a DU145 cell-coated Dynatech plate and incubated for one hour at room temperature (R.T.). Isotyping reagents in the form of rabbit anti-mouse immunoglobulin were added and the plates incubated for 1 hour at R.T. Horseradish peroxidase conjugated (HRPO) goat anti-rabbit IgG in 1% BSA-PBS-Tween was added and the plates were incubated for one hour at R.T. The PR92 monoclonal antibody proved to be isotype $IgG_1$.

In order to type the light chain, monoclonal antibody was added to DU145-coated plates and incubated for 2 hours at R.T. Rabbit antiserum against mouse kappa light chain and goat antiserum against mouse lambda light chain were added to separate wells. The plates were incubated for an additional 1 hour at R.T. HRPO goat anti-rabbit IgG and HRPO rabbit anti-goat IgG were added, respectively, and the mixtures were incubated for one hour at R.T. The monoclonal antibody proved to contain a kappa light chain.

The $IgG_1$ monoclonal antibody produced by cell line H92C149 was designated "PR92" monoclonal antibody.

EXAMPLE 3

Radioimmunoassay Utilizing PR92 Monoclonal Antibodies for Detection of Tumor-Associated Antigens Mouse ascites fluid containing PR92 monoclonal antibody (Mab) produced by cell line H92C149 (ATCC HB 9390) was harvested and pooled. The gamma fraction of the proteins containing PR92 Mab were prepared using ammonium sulfate fractionation in one-half saturated ammonium sulfate concentration. PR92 Mab was labeled with $I^{125}$ using the chloramine T procedure. "Removawell" titration plates (Dynatech) were coated with the unlabeled gamma fraction (40 μg/ml) from the ammonium sulfate cut and overcoated with 1% BSA. The plates were washed twice with 0.05M PBS containing 0.1% Tween 20 (PBS-Tween). Diluted standard and unknown specimens in 1% BSA-PBS-Tween buffer solution were contacted with the PR92 Mab-coated wells. All wells were incubated for 3 hours at room temperature, then washed twice with PBS-Tween. $I^{125}$-labeled PR92 Mab, prediluted in 1% BSA-PBS-Tween buffer, was contacted with the plates for 2 hours at R.T. The plates were washed three times with PBS-Tween and each well was counted for γ-radioactivity. The calculation of results was executed using a constructed standard curve.

In order to determine the specificity of the PR92 Mab radioimmunoassay, a number of cancer cell markers were tested. These included the DU145 cell extract and prostatic acid phosphatase (PAP), one of the presently utilized "markers" for prostate cancer. Also included were: prostate specific antigen (PA); carcinoembryonic antigen (CEA); alfa-fetoprotein; ferritin; blood group substances (A, B, H, T); the Centocor commercial assay antigens CA 19-9, CA 125, and CA 15-3; Human actin; Fibrinogen; Human colonic mucin; Seminal plasma; and β-2 Microglobulin. The results shown in Table III indicate that the radioimmunoassay specifically detects antigens present in the DU145 cell extract.

TABLE III

Detection of Tumor-associated Markers Using PR92 Mab Radioimmunoassay

| Marker | Detection | Highest concentration tested |
| --- | --- | --- |
| DU145 cell extract | + | Cell extract |
| Prostatic acid phosphatase | − | 30 ng/ml |
| Prostate specific antigen | − | 50 ng/ml |
| Carcinoembryonic antigen | − | 60 ng/ml |
| Alfa-fetoprotein | − | 40 ng/ml |
| Ferritin | − | 400 ng/ml |
| Human blood group substance A,B,H,T. | − | Erythrocyte extract |
| CA 19-9 | − | 120 units/mL |
| CA 125 | − | 500 units/mL |
| CA 15-3 | − | 200 units/mL |
| Human actin | − | 50 ug/mL |
| Fibrinogen | − | 1 ug/mL |
| Human colonic mucin | − | 1 ug/mL |
| Seminal plasma | − | 10-fold dilution |
| $\beta$-2 Microglobulin | − | 2 ug/mL |

EXAMPLE 4

Measurement of Antigens in Urine Specimens from Patients with Prostate Cancer using the PR92 Mab Radioimmunoassay Urine samples from normal subjects and from patients with benign prostate disease, prostate cancer, benign bladder disease and bladder cancer were tested using the labeled PR92 Mab RIA. The radioimmunoassay methodology used in example 3 was employed. The results indicate that increased amounts of antigens reactive with the PR92 Mab were present in urine samples of prostate cancer patients as compared to those of normal or benign disease controls.

EXAMPLE 5

Measurement of Antigens in Serum Specimens from Patients with Prostatic Cancer Using the PR92 Mab RIA Serum samples from 58 males, clinically classified as having normal prostate glands were assayed using the PR92 Mab RIA of example 3, as were serum samples from 29 males clinically classified as having benign prostate disease and 31 males clinically diagnosed as having prostate cancer. The results of the assays are graphically represented in FIG. 1. Of the samples from normal males, only one displayed reactivity at a level significantly higher than that displayed by other normal and benign disease patient samples. Twenty-three of 31 samples from the prostate cancer group displayed reactivity above a 5 Unit/ml level.

A correlative study of serum samples from normal males and males diagnosed for benign prostate disease or for prostate cancer was performed using the prostatic acid phosphatase (PAP) enzyme immunoassay. Nine of sixty normal male serum samples displayed PAP levels in excess of the baseline level ordinarily delineating "positive" and "negative" results. Similarly elevated PAP levels were detected in two of twenty-eight serum samples from benign prostate disease patients. In contrast to the PR92 Mab assay study, only sixteen of the thirty-one prostate cancer patient serum samples tested as "positive" according to the PAP assay.

The above results indicate a higher degree of specificity and sensitivity in prostate cancer detection using the PR92 Mab RIA rather than using the PAP enzyme immunoassay.

EXAMPLE 6

Measurement of Antigens in Serum of Patients with a Variety of Cancers and Benign Diseases Using the PR92 Mab Radioimmunoassay Serum samples from patients with cancer of the kidney, ovary, bladder, liver, thyroid, colorectum, esophagus, stomach, brain, head, neck and cervix, as well as sera from patients with a melanoma and leukemia were tested using the RIA of example 3. Also tested were serum samples from patients with benign diseases of the ovary, lung and liver. Results indicated decreased amounts of antigens reactive with PR92 Mab as compared, for example, to the serum samples from patients with breast cancer as described in example 7, infra.

EXAMPLE 7

Figure 2:
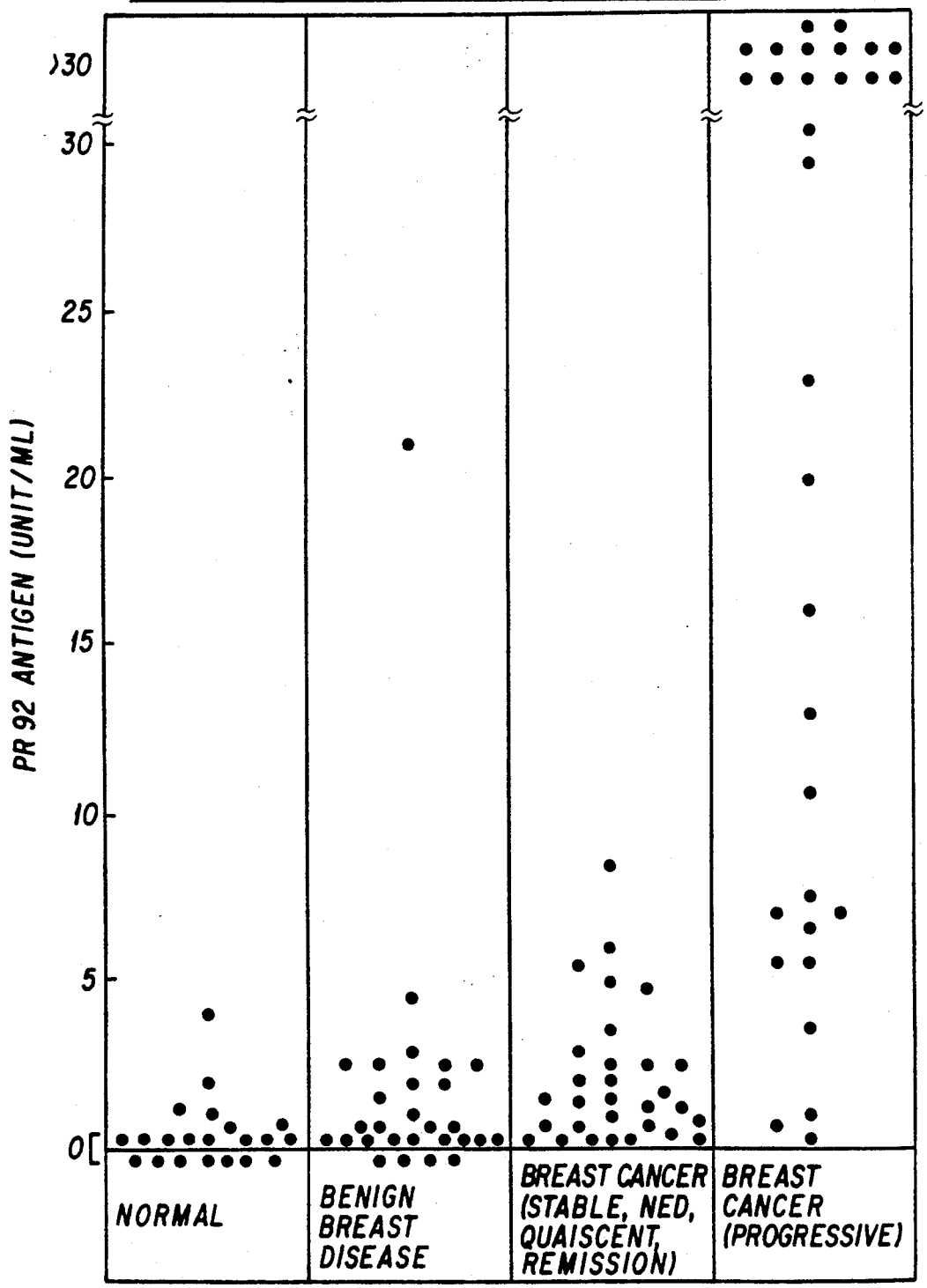

Comparison of the PR92 RIA and the CEA Assay in Detection of Breast Cancer Patients Serum samples from 110 patients were assayed by the PR92 Mab RIA of example 3 and the results are graphically represented in FIG. 2. Of twenty-one samples of sera from normal subjects, no sample displayed reactivity above a value of 5 Units/ml. In 28 samples of sera from patients diagnosed as having benign breast disease, one sample displayed reactivity above 5 Units/ml. In 30 samples of serum from patients with breast cancers which were clinically established to be stable, quiescent or in remission, three samples displayed a reactivity level greater than 5 Units/ml. Of 31 samples of serum from patients clinically diagnosed as having breast cancer, twenty seven samples demonstrated reactivity levels above 5 Units/ml.

In a correlated test of serum samples based on detection of carcinoembryonic antigen (CEA), none of the normal sera displayed reactivity above a baseline value of 5 ng/ml. In 29 serum samples from breast cancer patients clinically designated to be stable, quiescent or in remission, 7 of the 29 exhibited CEA levels above the baseline value. In serum samples from patients clinically diagnosed as having breast cancer, only 9 of 22 demonstrated CEA levels above the baseline.

The above results indicate a higher degree of specificity and sensitivity in breast cancer detection for the PR92 Mab RIA than for the CEA immunoassay.

EXAMPLE 8

Measurement of Antigens in Pleural Effusions Using PR92 Mab Radioimmunoassay

Pleural fluids from patients with breast, esophageal, kidney and lung carcinomas, lymphoma, adenocarcinoma of unknown primary site and mesotheliomas were screened using the PR92 Mab RIA of example 3. The pleural effusion samples of the adenocarcinoma patients and those of breast carcinoma patients reacted with the PR92 monoclonal antibody to a greater degree than specimens from the other patients.

EXAMPLE 9

Characterization of PR92 Antigen Compositions

"PR92 antigen" compositions were purified and isolated from collected pleural fluids of patients with adenocarcinomas of unknown primary origin, using affinity chromatography utilizing agarose-conjugated PR92 Mab produced by cell line H92C149 (ATCC HB 9390). Antigen was eluted using phosphate/citrate buffer (0.1M/0.1M), pH 3.0. Preliminary molecular weight analysis of the affinity purified antigen compositions by Western Blot of the material in "native" form in SDS revealed a band in excess of 200 kD and smaller bands of 174±7 kD, 149±2 kD, 123±5 kD, 87±5 kD, and 40±4 kD bands. Upon reduction of the composition with β-2-mercaptoethanol, Western Blot analysis again revealed a band in excess of 200 kD and a single band at 47 kD. High performance liquid chromatography (HPLC) of the antigen composition revealed a major active peak at 480±10 kD.

The stability of antigenic sites (epitopes) of antigens recognized by the PR92 Mab was studied using the following procedures. After treatment in 0.6M perchloric acid the composition retained 99% of its antigenicity as measured with the PR92 Mab RIA. The PR92 antigen compositions retained antigenicity upon heat treatment in 0.1M sodium acetate at 100° C., pH 5.5, for 2 minutes. However, acid/heat treatment with 0.05M $H_2SO_4$ at 80° C. for ¼ hour or neuraminidase treatment at 37° C., pH 5.0, for 52 hours resulted in complete loss of reactivity with the PR92 Mab. Treatment with lactase (Sigma Chemicals, St. Louis) by incubation of 10 units of purified PR92 antigen composition with 32 units of enzyme at pH 5.0, for 16 hours at 37° C. resulted in loss of 67% of antigenicity, indicating involvement of β-D-galactose at the relevant epitope(s). The PR92 antigen composition maintained 10–20% reactivity with PR92 Mab after trypsin treatment at 37° C., pH 7.0, for 52 hours. It was projected from the results of these experiments that the PR92 antigen composition includes glycoproteins and that the carbohydrate moieties are relevant to the epitope(s) recognized by the PR92 Mab.

Inhibitory binding studies using PR92 antigens and a radioimmunoassay utilizing a number of lectins and carbohydrates suggested that the relevant epitope(s) of the glycoproteins include side chains composed of sialic acid and N-acetyl-β-D-galactosamine. Tables IV and V demonstrate that sialic acid and five lectins with carbohydrate moieties consisting of sialic acid or N-acetyl-β-D-galactosamine interfered with the binding between PR92 Mab and the PR92 antigen compositions.

TABLE IV

Inhibitory Property of Lectins and Carbohydrates in PR92 Radioimmunoassay

| Lectin or Carbohydrate | Carbohydrate Specificity | Inhibition with PR92 antigen |
|---|---|---|
| D-Galactose | D-Gal | — |
| N-Acetyl Galactosamine | Gal.NAC. | — |
| N-Acetyl Glucosamine | Glc.NAc. | — |
| Lactose | Lactose | — |
| Sialic acid | Sialic acid | + |
| Arachis Hypogaea (PNA) | D-Gal, β-D-Gal.NAc. | + |
| Bandeirea Simplicifolia (GS-I) | D-Gal. | — |
| Bandeirea Simplicifolia (GS-II) | D-Gal.NAc. | — |
| Bauhinia Purpurea (BPA) | D-Gal.NAc. | + |
| Canavalia Ensiformis (ConA) | α-D-Mannose.Glc. | — |
| Dolichos Biflorus (DBA) | α-D-Gal.NAc. | — |
| Glycine Max (SBA) | α,β-Gal.NAc. | — |
| Helix Pomatia (HPA) | α-D-Gal.NAc. | — |
| Limax Flavus Aggl. (LFA) | Sialic acid | + |
| Maclura Pomifera (MPA) | α-D-Gal | — |
| Sophora Japonica (SJA) | α-D-Gal.NAc. | — |
| Triticum Vulgaris (WGA) | β-D-Glc.NAc., Sialic acid | + |
| Ulex Europaeus (UEA-1) | α-L-Fucose | — |
| Wistaria Floribunda (WFA) | D-Gal.NAc. | — |

TABLE V

Inhibitory Properties of Human Blood Group Antigen

| Blood group substance | Inhibition of binding between PR92 antigen and PR92 Mab |
|---|---|
| A | — |
| B | — |
| D | — |
| M | — |
| N | — |
| TF | — |

TF: Thomson-Friedenrich antigen.

Amino acid analysis was performed on three samples of the PR92 antigen. Table VI gives the average values determined for the content of each amino acid in this antigen.

TABLE VI

Average Amino Acid Analysis of PR92 Antigen

| Amino Acid | Relative Content*** |
|---|---|
| Aspartic Acid | 0.44 |
| Threonine | 0.72* |
| Serine | 0.78 |
| Glutamic Acid | 0.45 |
| Proline | 0.97 |
| Glycine | 0.75 |
| Alanine | 1.00 |
| Cysteine | 0.05* |
| Valine | 0.37 |
| Methionine | 0.06* |
| Isoleucine | 0.06 |
| Leucine | 0.18 |
| Tyrosine | 0.06 |
| Phenylalanine | 0.09 |
| Histidine | 0.24 |
| Lysine | 0.15 |
| Tryptophan | 0.00 |
| Arginine | 0.26 |

*Extrapolated value from kinetic hydrolysis data.
**Estimated N-acetyl glucosamine content is 0.76 and N-acetyl galactosamine content 0.65.
***These values were normalized with respect to the alanine value.

The molecular weight of PR92 antigen from patients with breast cancer, prostate cancer, adenocarcinoma, and from DU145 cell extract and DU145 tissue culture medium, were determined by high performance liquid chromatography. Table VII demonstrates the narrow range of molecular weights that were determined for the antigen even though it was found in various sources.

TABLE VII

Molecular Weight of PR92 Antigen Present in Different Specimens, Detected by HPLC

| Sample | No. of Sample | Apparent Molecular Wt. |
|---|---|---|
| PR 92 antigen (DU145 tissue culture media, purified) | 3 | 473 ± 15 KD |
| Serum (Breast Cancer) | 2 | 450 ± 14 |
| Serum (Prostate Cancer) | 4 | 463 ± 14 |
| Urine (Breast Cancer) | 2 | 470 |
| Urine (Prostate Cancer) | 2 | 470 ± 50 |
| Pleural Fluid (Adenocarcinoma) | 3 | 465 ± 41 |
| DU145 cell extract | 1 | 470 |

EXAMPLE 10

The Use of PR92 Mab Radioimmunoassay as a Prognostic Indicator

In one series of experiments, serum samples of five prostate cancer patients were collected over periods ranging from 108 to 719 days, stored at $-20°$ C., and analyzed for PR92 antigen content. The results were correlated to clinical evaluations of the disease state of the patient at the time of sampling. In two instances correlations were also made to results obtained using assays for PAP and PA, commercially available from Abbott Laboratories, North Chicago, Ill. (PAP) and Cetus Corporation, Emeryville, Calif. (PA). The resulting data are set forth in FIGS. 3, 4 and 5.

The clinical evaluations, where known, are abbreviated: progressive (PRO), stable (ST), remission (REM), response to a treatment (RES) and no evidence of disease (NED). Where available, days are indicated on abscissas.

Figure 3:
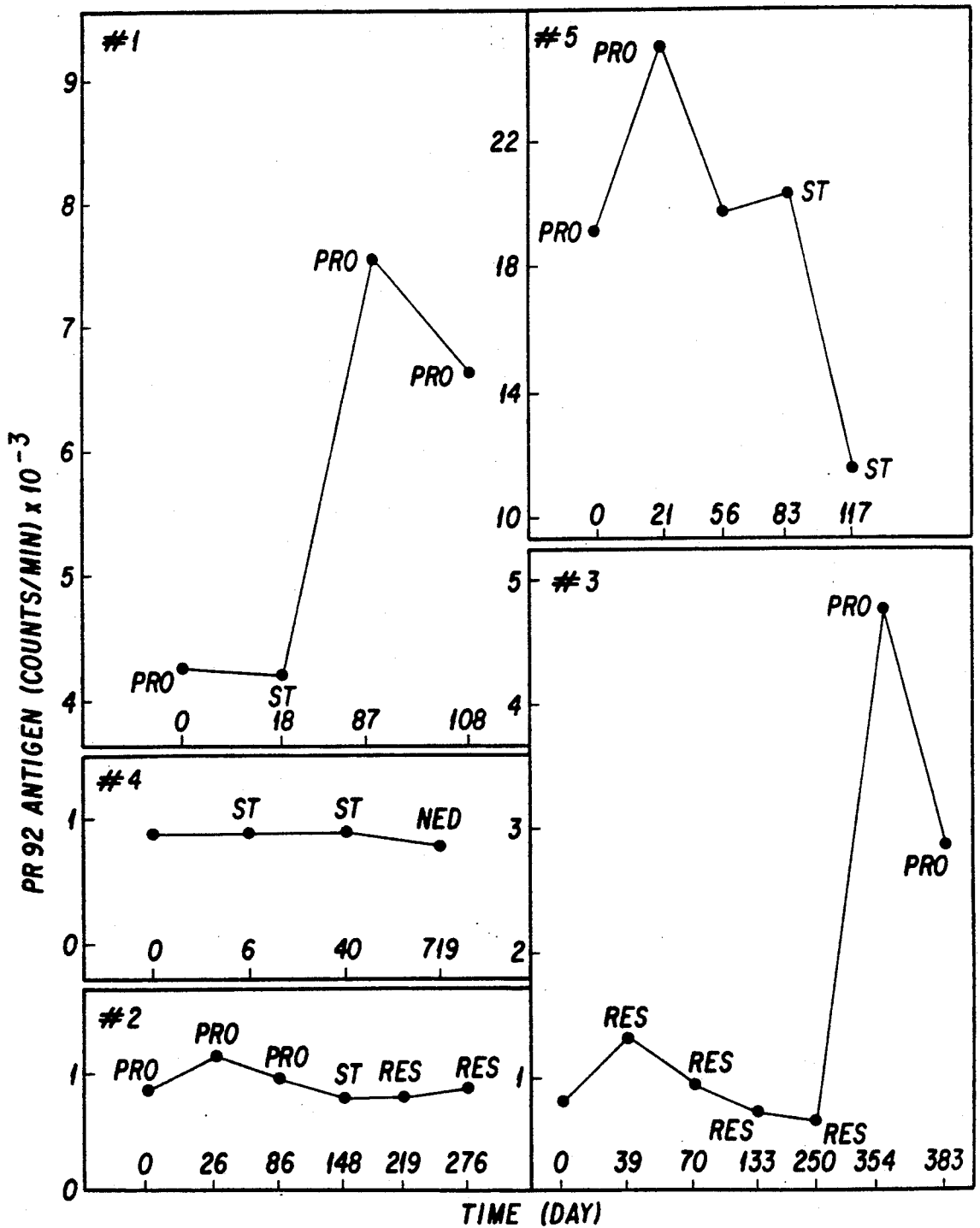
Figure 4:
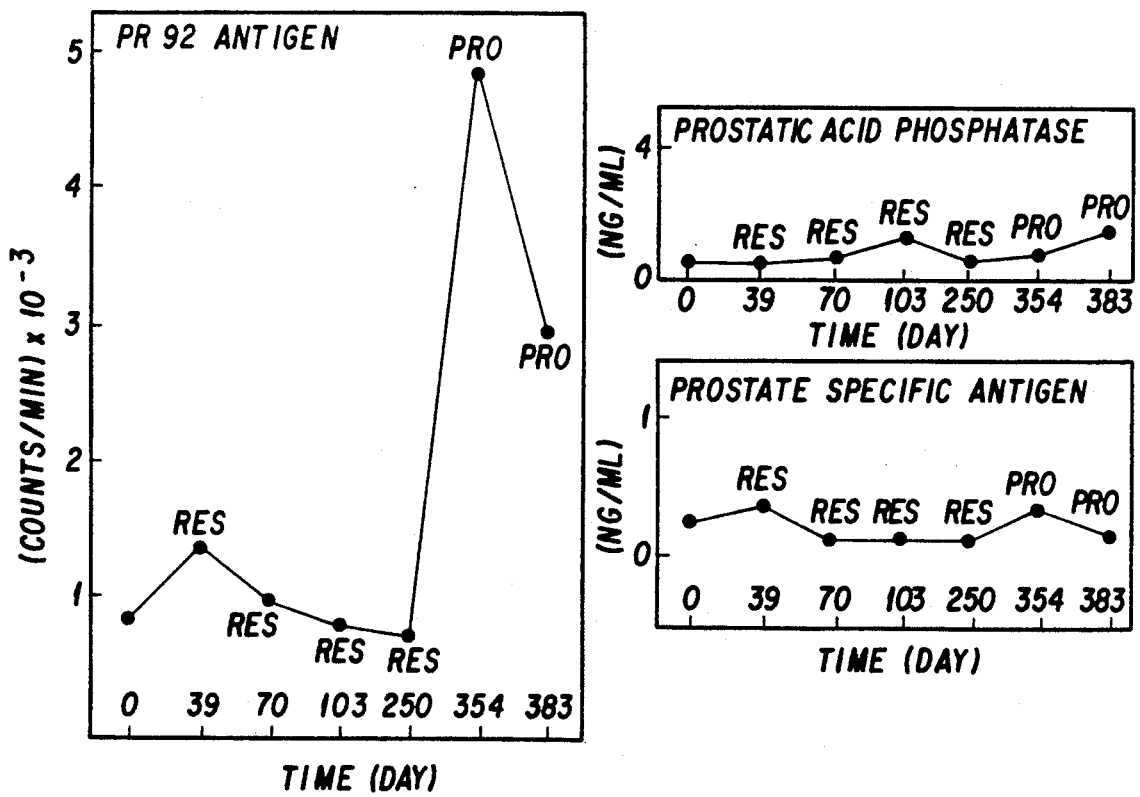
Figure 5:
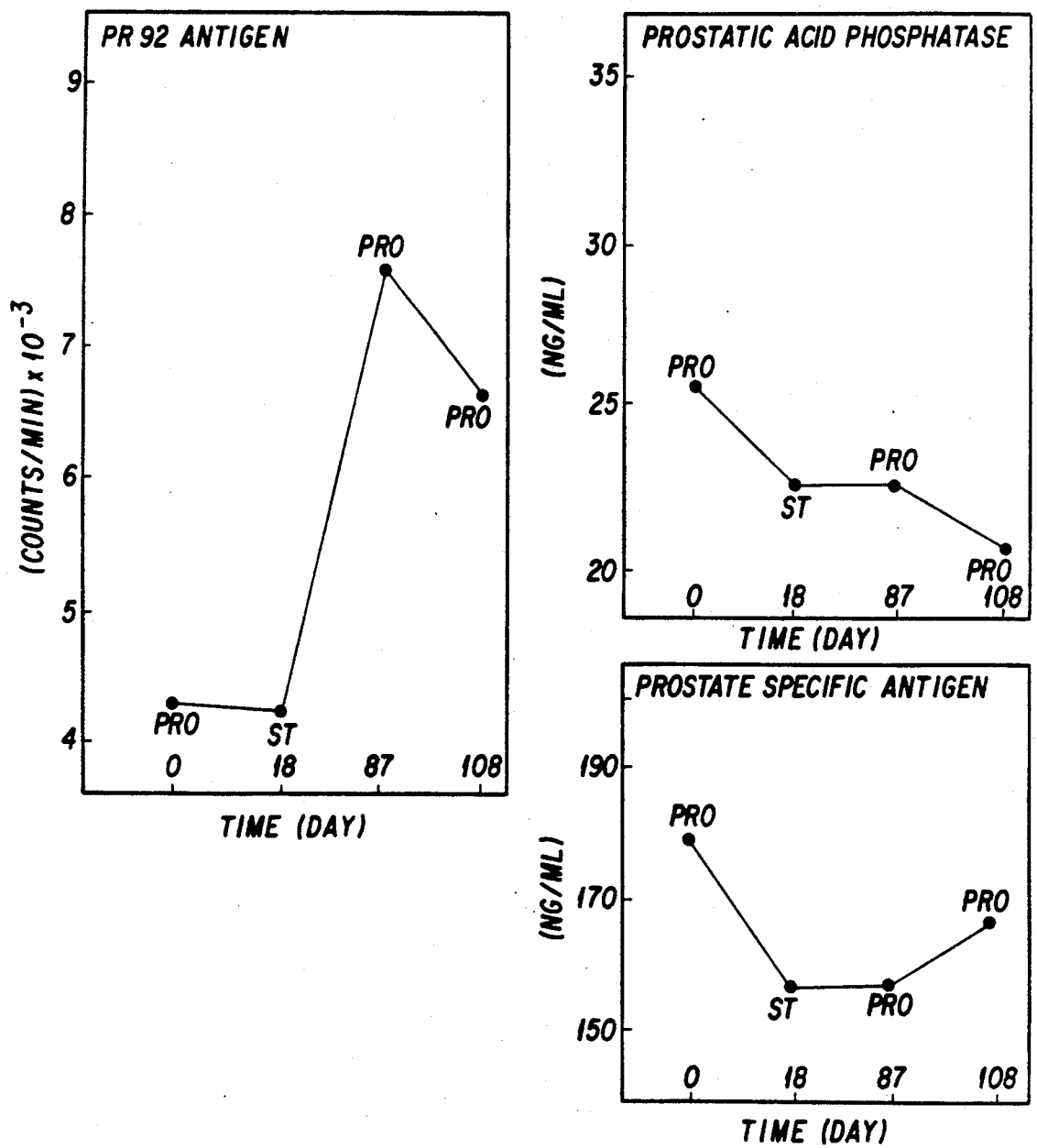

The data set forth in FIGS. 3, 4, and 5 reveal a high degree of correlation between serum PR92 levels and the clinical evaluations. Significantly, no similar correlations could be drawn with respect to the PAP and PA test results.

In a similar manner, serum samples from patients with breast cancer taken at clinically relevant times and, as indicated in FIG. 6, also showed that the clinical evaluation of the disease state was readily correlatable to the results of the PR92 Mab RIA.

It is also of significance that analysis of sera from 10 breast cancer patients clinically evaluated as being in a "Stage IV" disease state revealed highly elevated PR92 levels ranging from a minimum of 10 Units/ml to in excess of 50 Units/ml. These studies indicate that the sensitivity of the PR92 Mab RIA is such that it can be useful as a diagnostic and also as a prognostic indicator of a breast cancer disease state.

In this respect it is noteworthy that preliminary comparative screening of purified and isolated PR92 antigen compositions revealed total binding to the PR92 Mab and strong binding with the monoclonal antibodies of cell lines H92C152 and H23C136. Moderate binding of the antigen compositions was noted with the Centocor commercial assay kit 115D8 monoclonal antibody to the tumor-associated CA 15-3 antigen but no binding between the PR92 antigen composition and the DF-3 monoclonal antibody to the same CA 15-3 antigen was observed. The preliminary binding studies also revealed a lack of binding between the PR92 antigens and the B72.3 monoclonal antibody described in Nuti, et al., *Int. Jour. Cancer*, 29, 539–545 (1982).

EXAMPLE 11

PR92 Antigen From DU145 Cell Extract

An alternate, non-human, source of PR92 antigen was developed from the soluble cell extract from DU145 cells. Starting with approximately $100 \times 10^6$ cultured DU145 cells in 25 milliliters of cell medium, phosphate buffered saline solution was added to a final volume of 50 mls., then centrifuged for 5 minutes at 1500 rpm, at room temperature. The supernatant was decanted and the cells resuspended in 10 ml of a buffer consisting of 0.15M NaCl, 0.04M EDTA, 0.04M Tris, 0.2 mM PMSF, and 0.5%(w/v) NP40, at a pH of 7.0. The suspended cells were aliquoted in two $\frac{5}{8}'' \times 3''$ centrifuge tubes and placed in an ice bath at $4°$ C. for 1 hour, vortexed occasionally to keep the cells in suspension, then centrifuged for 1 hour at 40,000 rpm, equilibrated at $4°$ C. Both supernatants were combined and dialyzed against phosphate buffered saline solution overnight at $4°$ C. The dialyzed solution was centrifuged for 15 minutes at 12,000 rpm, equilibrated at $4°$ C.

The PR92 antigen was isolated and purified by the following method. PR92 monoclonal antibodies were coupled to Sepharose 4B and packed on an immunoaffinity column. The cell extract solution of above was applied to the immunoaffinity column and eluted with phosphate buffered saline solution, pH 7.4, at room temperature. Using phosphate-citrate buffer, pH 3.0, the column was rinsed and the bound PR92 antigen was eluted. The eluent was immediately neutralized to pH 7, and dialyzed against phosphate buffered saline solution overnight at $4°$ C.

The molecular weight of the intact PR92 antigen was determined to be $4.7(\pm 0.3) \times 10^5$ by high performance liquid chromatography. Western blot analysis and disc gel electrophoresis in the presence of sodium decyl sulfate and a reducing agent revealed that the PR92 antigen is a multimer, comprised of $43(\pm 3)$ kD subunits. The presence of the PR92 monoclonal antibody binding epitope in each subunit was confirmed.

EXAMPLE 12

PR92 Antigen from DU145 Cell Tissue Culture Medium

The PR92 antigen was also discovered in DU145 cell tissue culture medium. DU145 cells were planted at a concentration $5 \times 10^6$ cells/50 ml of Minimum Essential Media with 10% fetal bovine serum in a 150 cm$^2$ flask under $CO_2$ and incubated for 24 hours at $7°$ C. The flask was transferred to a $37°$ C. incubator and incubated for one week. Then the medium was decanted and 100 ml of Minimum Essential Media with 1% fetal bovine serum was added to the flask. The flask was incubated for 3 weeks at $37°$ C., and then the DU 145 tissue culture medium was harvested.

The antigen was isolated and purified as in Example 11. The molecular weight was the same as that of the antigen in Example 11.

EXAMPLE 13

PR92 Antigen from CHAGO Tissue Culture Medium

A PR92 antigen like antigen was found in the tissue culture medium of CHAGO cells, which are derived from lung cancer cells. Approximately $5 \times 10^6$ CHAGO cells/50 ml of PRMI HEPES-FBS medium were planted in a 150 cm² flask under $CO_2$ and incubated for 24 hours at 37° C. Next, the flask was incubated at 37° C. for one week. The medium was decanted and 100 ml of minimum essential media with 1% fetal bovine serum was added to the flask. The cells were incubated for 3 weeks at 37° C., and then the CHAGO tissue culture medium was harvested.

The antigen was isolated and purified as in Example 11, and then was further purified by passing the eluent through a Sephacryl S-200 chromatography column. Each fraction then had its antigen level monitored with a radioimmunoassay procedure using the PR92 monoclonal antibody. All fractions exhibiting significant antigen levels were combined and the molecular weight of the antigen was determined to be approximately $6.0 \times 10^5$. Although the molecular weight of this antigen is greater than that of the PR92 antigens recovered from pleural fluid, DU145 cells and DU145 cell tissue culture medium, this antigen is believed to be substantially similar to the others because of its reactivity with the very specific PR92 monoclonal antibody.

The foregoing illustrative examples are believed to provide a demonstration of the value of the monoclonal antibodies produced by hybridoma cell ATCC HB 9390 as an aid in the diaqnosis and clinical monitoring of patients suffering from prostate and breast cancer disease states. It will be understood that duplication of the hybridoma generating and antibody screening procedures as set forth in example 1 can be expected to give rise to other cell lines producing monoclonal antibodies immunoreactive with the same antigenic sites as PR92 Mab (as may be determined, e.g., by competitive binding studies) and/or antibodies immunoreactive with other epitopes of the same antigen. It will also be apparent that the novel purified and isolated PR92 antigen compositions provided by the invention may readily be employed in antibody screening and to generate polyclonal and monoclonal antibodies having the same or different affinity or specificity as PR92 Mab and having similar utility as an aid in the diagnosis and prognosis of prostate and breast cancer disease states.

Thus, while the illustrative examples deal principally with single antibody assays, multiple antibody assays (including, e.g., two monoclonal antibodies, two polyclonal sera, or a monoclonal antibody and polyclonal antibodies) are within the contemplation of the invention, as are heterologous assays employing combinations immunological reagents associated in the art with breast and/or prostate cancers.

While preliminary histological assays of reactivity of PR92 Mab with a variety of normal and tumor cells failed to establish substantial selectivity of the antibody for breast and prostate tumor cells, it is nonetheless contemplated that antibodies of the invention (especially antibodies other than PR92 Mab) may be useful in histological screening assays and possibly even in therapeutic regimens based on use of antibodies for delivery of therapeutic agents to tumor cells.

Numerous modifications and variations in the practice of the invention are expected to occur to those skilled in the art and consequently only such limitations as appear in the appended claims should be placed thereon.

I claim:

1. In a method for determining the presence of a prostate or breast cancer disease state in a human patient wherein a patient body fluid sample is subjected to analysis for detection of a tumor-associated antigen, wherein the improvement comprises analyzing said fluid sample for the presence of the tumor-associated antigen, specifically immunoreactive with the monoclonal antibody produced by murine derived hybridoma cell line ATCC HB 9390 and having a molecular weight of about 420,000 to about 520,000 daltons under non-reducing conditions, and thereby determining the presence of a prostate or breast cancer disease state.

2. The method of claim 1 wherein the body fluid sample analyzed is a serum sample.

3. The method of claim 1 wherein the body fluid sample analyzed is a urine sample.

4. The method of claim 1 wherein said analysis step comprises an immunoassy selected from the group consisting of a radioimmunoassay, an enzyme-linked immunosorbent assay, and a fluorescent immunoassay.

5. A murine-derived hybridoma cell line ATCC HB 9390, wherein antibody produced by said cell line reacts with a tumor-associated antigen having a molecular weight of about 420,000 to about 520,000 daltons under non-reducing conditions.

6. A monoclonal antibody produced by hybridoma cell line ATCC HB 9390, wherein said antibody reacts with a tumor-associated antigen having a molecular weight of about 420,000 to about 520,000 daltons under non-reducing conditions.

7. A monoclonal antibody according to claim 6 to which a detectable label is attached.

8. A monoclonal antibody according to claim 7 wherein said label is selected from the group consisting of a radiochemical, an enzyme and a fluorescent compound.

9. An assay procedure for the detection of prostate or breast tumor-associated antigens in a fluid sample of a patient, said procedure comprising the steps of:

(a) incubating said fluid sample with a solid support to which monoclonal antibodies produced by hybridoma cell line ATCC HB 9390 have been affixed to form a first reaction mixture comprising said monoclonal antibodies and tumor-associated antigens bound thereto, wherein the tumor-associated antigens have a molecular weight of about 420,000 to about 520,000 daltons under non-reducing conditions;

(b) removing unbound components of said fluid sample from said first reaction mixture;

(c) incubating said first reaction with labeled monoclonal antibodies produced by hybridoma cell line ATCC HB 9390 to form a second reaction mixture;

(d) removing unbound labeled monoclonal antibodies from said second reaction mixture; and (e) determining the extent to which labeled monoclonal antibodies are bound in said second reaction mixture, thereby detecting prostate or breast tumor-associated antigens in the fluid sample.

10. A kit for detection of prostate or breast tumor-associated antigens having a molecular weight of about 420,000 to about 520,000 daltons under non-reducing conditions, comprising in containers:

(a) a monoclonal antibody produced by hybridoma cell line ATCC HB 9390 bound to a solid support; and (b) a labeled monoclonal antibody produced by hybridoma cell line ATCC HB 9390.

11. A purified and isolated PR92 tumor-associated antigen having a molecular weight of about 420,000 to about 520,000 daltons under non-reducing conditions, characterized by immunological reactivity with the monoclonal antibody produced by murine-derived hybridoma cell line ATCC HB 9390.

12. A purified and isolated tumor-associated antigen according to claim 11 derived from a human pleural fluid isolate and further characterized by a non-reduced molecular weight of up to about 480±10 kD and a reduced molecular weight of about 47 kd.

13. A purified and isolated tumor-associated antigen composition of claim 11 further characterized by the presence of one or more carbohydrate moieties selected from the group consisting of a sialic acid, an N-acetyl-beta-D-galactosamine, and a beta-D-galactose.

14. A method for determining the relative efficacy of a therapeutic regimen performed on a patient suffering from a prostate or breast cancer disease state, said method comprising:
  (a) initially analyzing a patient fluid sample to quantitatively detect tumor-associated antigens having a molecular weight of about 420,000 to about 520,000 daltons under non-reducing conditions, and immunoreactive with the monoclonal antibody produced by hybridoma cell line ATCC HB 9390; and
  (b) periodically repeating the analysis step (a) during the course of application of the therapeutic regimen to determine increases or decreases in quantity of tumor-associated antigens present in the sample.

15. A method for determining the recurrence of a prostate or breast cancer disease state in a patient clinically diagnosed as stabilized or in a remissive state, said method comprising:
  (a) initially analyzing a patient fluid sample to detect tumor-associated antigens having a molecular weight of about 420,000 to about 520,000 daltons under non-reducing conditions, and immunoreactive with the monoclonal antibody produced by hybridoma cell line ATCC HB 9390; and
  (b) periodically repeating the analysis step (a) to determine increases in the quantity of tumor-associated antigens present in the sample.

* * * * *